United States Patent [19]

Caprioli

[11] Patent Number: 5,078,135
[45] Date of Patent: Jan. 7, 1992

[54] APPARATUS FOR IN VIVO ANALYSIS OF BIOLOGICAL COMPOUNDS IN BLOOD OR TISSUE BY MICRODIALYSIS AND MASS SPECTROMETRY

[75] Inventor: Richard M. Caprioli, Houston, Tex.

[73] Assignee: Board of Regents, The University of Texas System, Austin, Tex.

[21] Appl. No.: 359,475

[22] Filed: May 31, 1989

[51] Int. Cl.$^5$ .............................................. A61B 5/00
[52] U.S. Cl. ............................................................ 128/632
[58] Field of Search ........................ 128/632, 635, 637; 604/4–6, 50–53, 65–67

[56] References Cited

U.S. PATENT DOCUMENTS

| | | |
|---|---|---|
| 3,649,199 | 3/1972 | Littlejohn . |
| 3,952,730 | 4/1976 | Key . |
| 4,123,353 | 10/1978 | Hakansson et al. ................ 128/632 |
| 4,253,456 | 3/1981 | Schindler et al. . |
| 4,633,878 | 1/1987 | Bombardieri ....................... 128/635 |
| 4,694,832 | 9/1987 | Ungerstedt ......................... 128/632 |
| 4,705,503 | 11/1987 | Dorman et al. ..................... 604/53 |
| 4,705,616 | 11/1987 | Andreson et al. . |
| 4,726,381 | 2/1988 | Jones ................................... 128/632 |
| 4,832,034 | 5/1989 | Pizziconi et al. ................... 128/632 |

FOREIGN PATENT DOCUMENTS

| | | |
|---|---|---|
| 0134758 | 3/1985 | European Pat. Off. . |
| 0211645 | 2/1987 | European Pat. Off. . |
| 2017907A | 10/1979 | United Kingdom . |

OTHER PUBLICATIONS

Brodbelt et al., "In Vivo Mass Spectrometric Determination of Organic Compounds in Blood with a Membrane Probe", Analytical Chemistry, vol. 59, No. 3, Feb. 1, 1987.

Urban Ungerstedt, "Microdialysis—A New Bioanalytical Sampling Technique", Current Separations, vol. 7, No. 2 (1986).

*Primary Examiner*—Ruth S. Smith
*Attorney, Agent, or Firm*—Arnold, White & Durkee

[57] ABSTRACT

The present invention combines microdialysis with mass spectrometry, for example continuous flow fast atom bombardment, to follow the pharmacokinetics of drugs or other compounds directly in the blood stream or tissues of a live animal. After intramuscular injection of the drug, the blood dialysate from a microdialysis probe inserted into a blood vessel or tissue of the animal, is allowed to flow into the mass spectrometer via the continuous flow fast atom bombardment interface. Tandem mass spectrometry allows for isolating and recording the ion fragments produced from the drug as the dialysate is exposed to the ionization process. The detected concentration of the drug or other compounds of interest can be used to adjust the rate of administration of the drug.

3 Claims, 3 Drawing Sheets

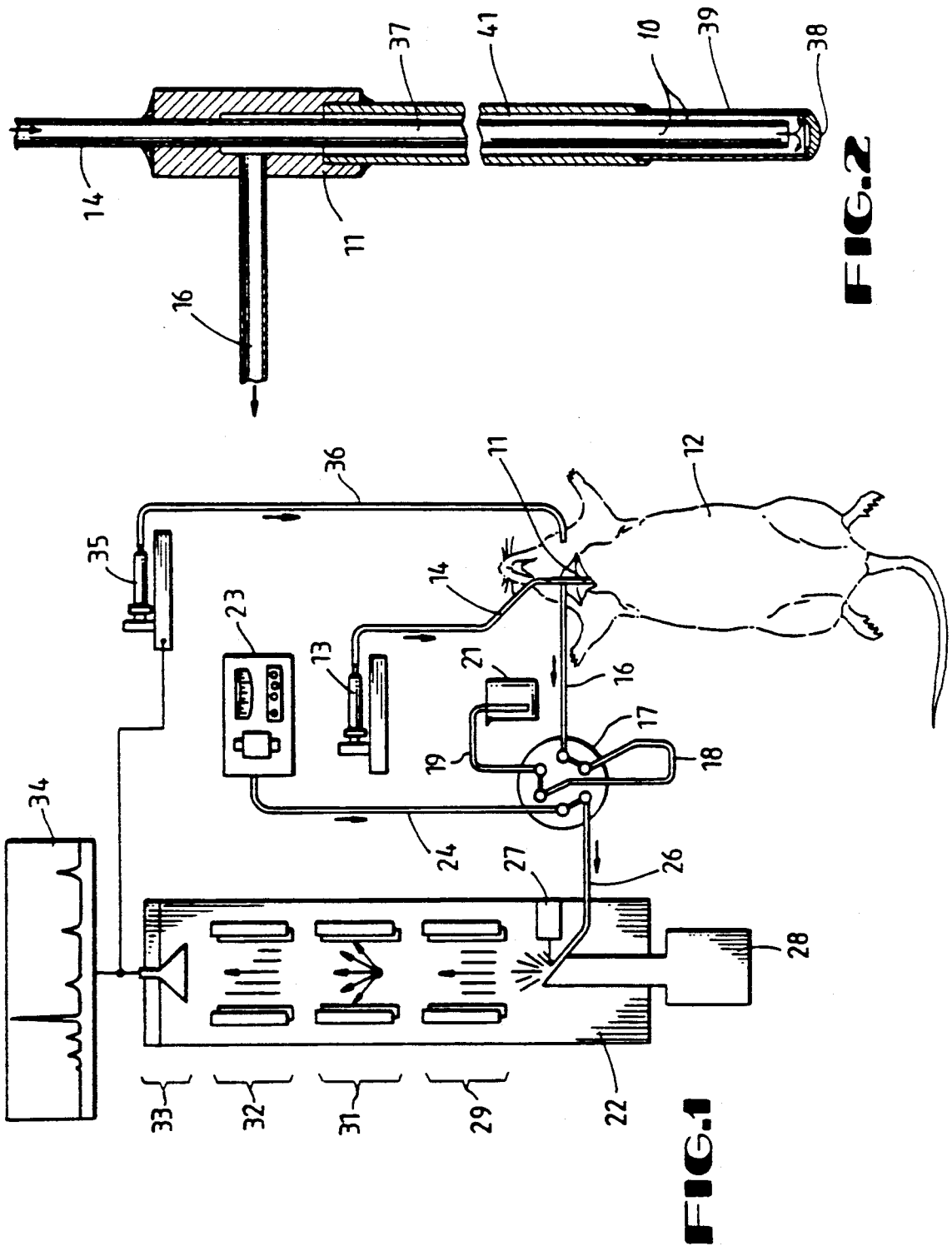

APPARATUS FOR IN VIVO ANALYSIS OF BIOLOGICAL COMPOUNDS IN BLOOD OR TISSUE BY MICRODIALYSIS AND MASS SPECTROMETRY

BACKGROUND OF THE INVENTION

The invention relates to an apparatus and method for the determination of concentrations of biological compounds, such as drugs and their metabolites, in vivo using microdialysis in combination with mass spectrometry.

Sepsis is a major problem in surgical critical care today. Infections, septic shock and multiple organ failure attributed to overwhelming sepsis are among the leading causes of complications, death and excessive financial burdens in tertiary surgical intensive care units. While surgical drainage and debridement techniques are often essential in control of sepsis, antibiotic infusions are usually relied upon as a cornerstone of therapy.

The development and availability of new drugs such as antibiotics and immunosuppressive agents have revolutionized the approach of modern medicine to the treatment of many conditions and diseases. The potency of many new antibiotics is extremely high and they are effective against many new resistant strains. Unfortunately, many of these drugs are also toxic to man and have deleterious effects on various organs and systems in the body. In addition, their metabolic fates can be complex, with some of the metabolites having strong physiological effects as well. This has resulted in many, if not most, critically ill patients being actually underdosed with regard to the antibiotic levels required for optimal inhibition of bacterial growth.

The determination of blood levels of these powerful new therapeutic agents and their metabolites is essential both in their clinical use and their use in the research laboratory. Methods which would allow such analyses in vivo and in real-time would be particularly advantageous in providing i) blood and/or tissue levels of patients during critical periods to maximize therapeutic value and minimize toxic effects, ii) tissue responses at specific sites in the body and in a time-course study, iii) verification of the presence and accumulation of intermediate metabolites which may have significant clinical implications, iv) improved quantification due to decreased sample handling losses and variable extraction efficiencies, and v) ease of use and time saving advantages because individual extraction, purification and derivatization steps are not required.

Modern mass spectrometric techniques, such as fast atom bombardment (FAB) mass spectrometry, offer unique analytical capabilities for quantification of drugs and their metabolites because they are effective in providing mass specific detection of compounds in complex mixtures derived from biological sources without the need for extraction and derivatization methods. However, samples for FAB analysis, for example, are typically prepared with high concentrations of glycerol or other suitable viscous liquids so that the samples remain in a liquid state during the introduction into the high vacuum chamber of the system throughout the analysis period. The presence of the added viscous liquid matrix results in several severe limitations including high background interfering solvent or matrix ion clusters, and relatively poor sensitivity.

SUMMARY OF THE INVENTION

In the disclosed embodiment, the present invention enjoys the advantage of FAB analysis without the above-mentioned disadvantages, by combining microdialysis with continuous flow fast atom bombardment (CF-FAB) to provide in vivo on line analysis of biological compounds, such as drugs and their metabolites. The microdialysis probe is implanted into a blood vessel or tissue of a live animal, and perfusate is passed through the probe and into a CF-FAB system. The invention can also be used to administer optimum doses of antibiotics, and the like, by adjusting an amount of drug being administered based on the CF-FAB analysis. Other mass spectrometric techniques are also usable in combination with microdialysis.

BRIEF DESCRIPTION OF THE DRAWINGS

FIG. 1 is the apparatus of the present invention being applied according to the method of the present invention to detect and control drug levels in a rat;

FIG. 2 is the microdialysis probe used in the present invention;

DETAILED DESCRIPTION OF THE PREFERRED EMBODIMENT

Figure 3A:
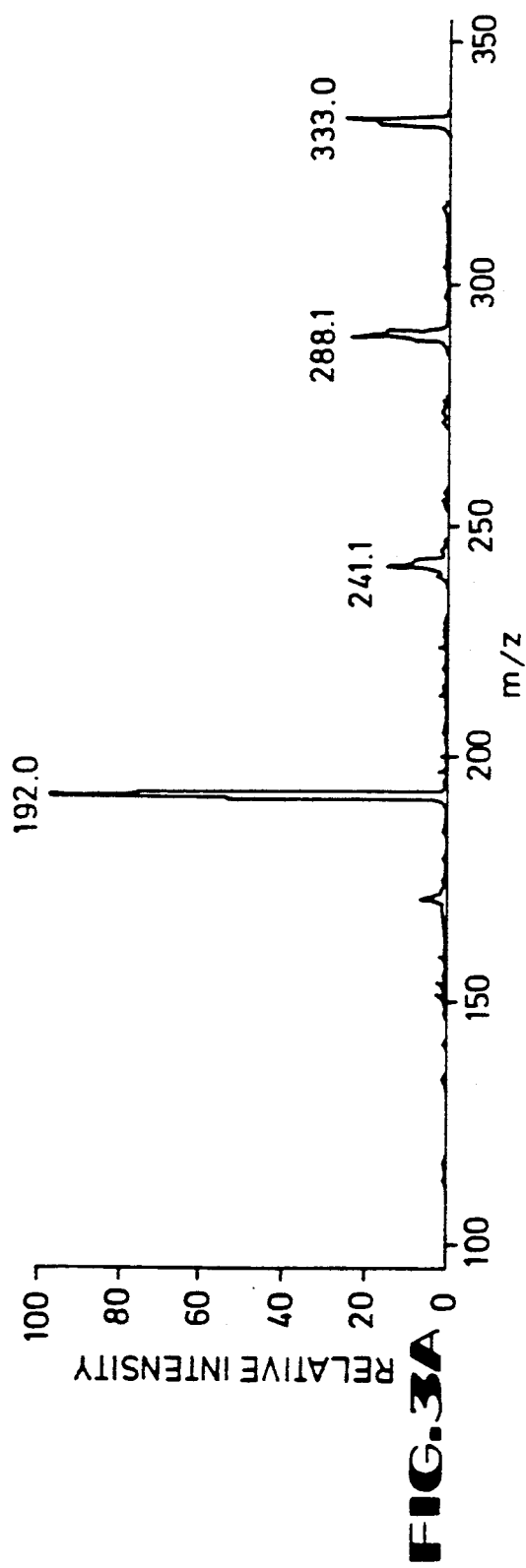
FIGS. 3A and 3B are graphs comparing the in vivo results of the present invention with in vitro results.

Referring to FIG. 1, the present invention applied to detect drug and metabolite levels in a rat is disclosed. It should be emphasized that the present apparatus and method can be applied to other animals, including humans. Microdialysis probe 11 is inserted inside a 22-gauge needle cannula (not shown) surgically placed in the jugular vein of a 330 gram Sprague Dawley male rat 12. A microliter syringe pump 13 is connected to microdialysis probe 11 by tube 14 and is used to controllably provide perfusate to microdialysis probe 11 through tube 14. Syringe pump 13 can be a Model 2274 pump available from the Harvard Apparatus Co., of Milford, Mass. In the preferred embodiment, the perfusate is 95% water and 5% glycerol provided at a rate of 4.8+/−0.2 microliters per minute.

The dialysate output from microdialysis probe 11 is connected through tube 16 to injection switch valve 17 which can be, for example, a Rheodyne Model 7410 injection switch valve. During collection, injection switch valve 17 is positioned so that dialysate passing through tube 16 passes through 20 microliter collection loop 18. Excess dialysate passes through waste tube 19 and is collected in waste container 21. Collection loop 18 may contain a trapping agent in order to purify and concentrate the biological compound of interest.

After dialysate is collected in collection loop 18 for approximately ten minutes, injection switch valve 17 is positioned so that the dialysate in collection loop 18 is forced into mass spectrometer 22 for approximately ten additional minutes with the aid of pump 23 and tubes 24 and 26, at a rate of approximately 4.6+/−1.8 microliters per minute. Pump 23 can be a Waters Model 590 HPLC pump.

Thus, the pharmacokinetic data is obtained through a series of collection/analysis cycles using sample collection loop 18 for a 20-minute total collection/analysis cycle time. Longer or shorter cycle times, or faster or slower perfusate and dialysate flow rates can be used without departing from the scope of the invention.

Mass spectrometer 22 is preferably a Finnigan MAT TSQ 70 mass spectrometer available from the Finnigan MAT Corp of San Jose, Calif. FAB mass spectrometer 22 includes a FAB gun 27 and a continuous flow FAB interface 28. The FAB ionization process gives rise to molecular $(M+H)^+$ or $(M-H)^-$ ions from all or most of the compounds in the continuously flowing sample. The molecular ion species of interest is selected by a first stage quadrupole 29 and is allowed to pass into collision region (second stage quadrupole) 31 where collision activated decomposition occurs as a result of collision of ions with argon gas admitted into region 31. The fragment ions produced in the collision activated decomposition process together with any surviving molecular ion species are then transmitted to third stage quadrupole 32 and then to ion detector 33 for detection and recording. The resulting mass spectrum 34 represents a specific fragment mass map of one specific molecular species which was selected by the first stage 29 of FAB mass spectrometer 22.

Automatic control of the administration of a drug can be accomplished by appropriately connecting the output of ion detector 33 to microliter syringe pump 35 which controls the rate of drug administration to rat 12 through tube 36. Pump 35 can also be a Model 2274 syringe pump available from Harvard Apparatus Co.

Referring now to FIG. 2, the details of microdialysis probe 11 used in the present invention are disclosed. Probe 11 includes an input tube 14 which is connected to an input portion of channel 10 of probe 11. Channel 10 of probe 11 includes perfusate channel 37, dialyzing membrane and channel 41. Perfusate flowing in tube 14 passes through perfusate channel 37 to the bottom portion 38 of probe 11. Perfusate then begins flowing upwardly in probe 11 past dialyzing membrane 39 and continues flowing upward through channel 41 and eventually exits probe 11 as dialysate through tube 16. When probe 11 is implanted in a blood vessel or tissue of a living animal, dialyzing membrane 39 acts to allow extraction of chemical substances from the living animal, without the removal of body fluids, through the process of diffusion of chemical substances from a relatively high concentration in the blood vessel or tissue to a relatively low concentration in the perfusate flowing in probe 11. The preferred source for microdialysis probe 11 is Bioanalytical Systems, Inc. of Lafayette, Ind.

FIG. 3A shows the negative ion mass spectrum of penicillin G taken during an in vivo test using the present invention of FIG. 1 approximately 1.5 hours after the administration of an intramuscular dose. The vertical axis of FIG. 3A is measured in units of relative intensity (intensity relative to the peak detected ion), and the horizontal axis is in units of mass-to-charge (m/z) ratio. The most intense ion at m/z 192 represents the major daughter ion of the parent $(M-H)^-$ ion. The proposed structure of this ion is:

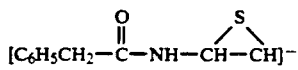

Figure 3B:
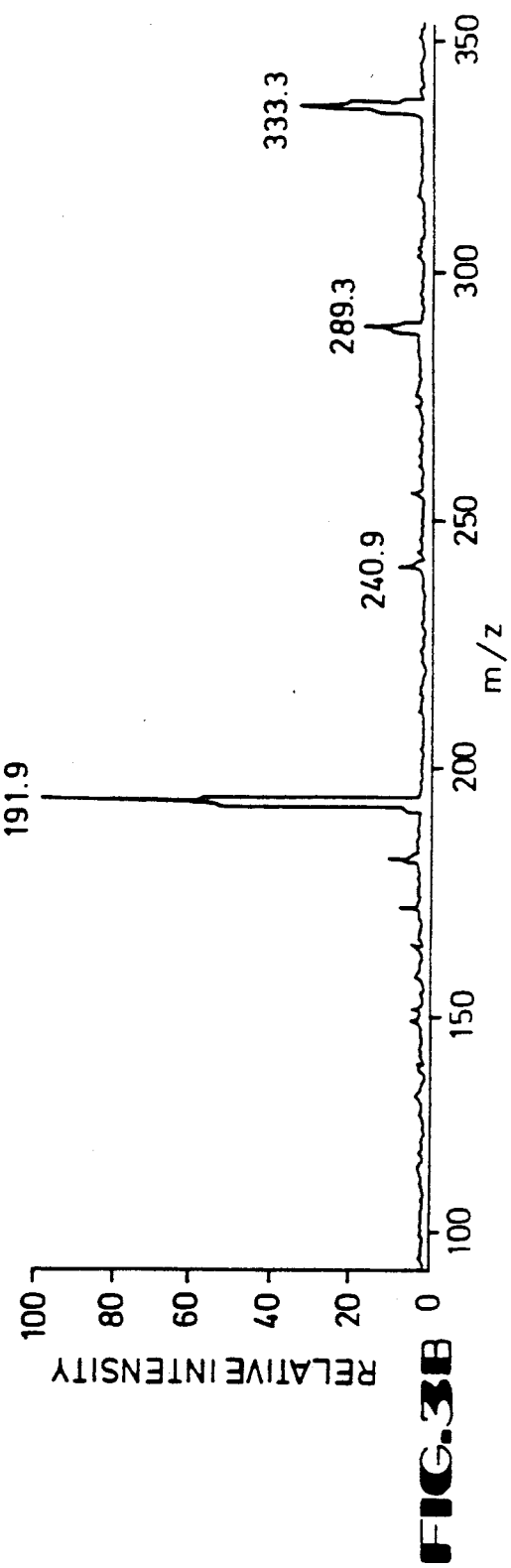

Some surviving $(M-H)^-$ molecular ion can be seen at m/z 333. For comparison, FIG. 3B shows the same spectrum, with identical axes, taken from the direct injection of penicillin G in a physiological saline. As can be seen, the spectra match quite well.

The efficiency of transfer of a drug in blood and subsequent analysis of the dialysate using the present invention is dependent on a number of factors. These include the time of exposure of a drug, the rate of perfusion of the microdialysis device, and the total sampling time. To determine the efficiency of the analysis of penicillin G under the experimental conditions used in the in vivo studies, a 1 milliliter portion of saline solution containing 30 micrograms of penicillin G was analyzed with the microdialysis device using the flow-injection method of the invention. Peak areas produced by monitoring the fragment ion at m/z 192 were measured, giving an average of $1.85 \times 10^5$ ion counts for three measurements. These measurements were repeated using a 20 microliter sample of the same solution for a sample injection, eliminating the microdialysis step. The average of three measurements gave peak areas of $1.16 \times 10^6$ ion counts. Thus, for this protocol, the recovery was calculated to be 15.9%. This compares favorably with the literature provided by Bioanalytic Systems which shows an average recovery of a number of low molecular weight compounds of about 14% at a 4 microliter per minute perfusion rate.

The linearity of the response of the analytical procedure of the present invention was measured by analyzing saline solutions containing 5, 10 and 30 micrograms per milliliter of sodium penicillin G. A linear response was observed, with the correlation coefficient for a linear least squares fit being 0.9889. A signal-to-noise ratio of 3.15 was recorded for analyses of samples of the antibiotic containing 5 micrograms per milliliter.

Figure 4:
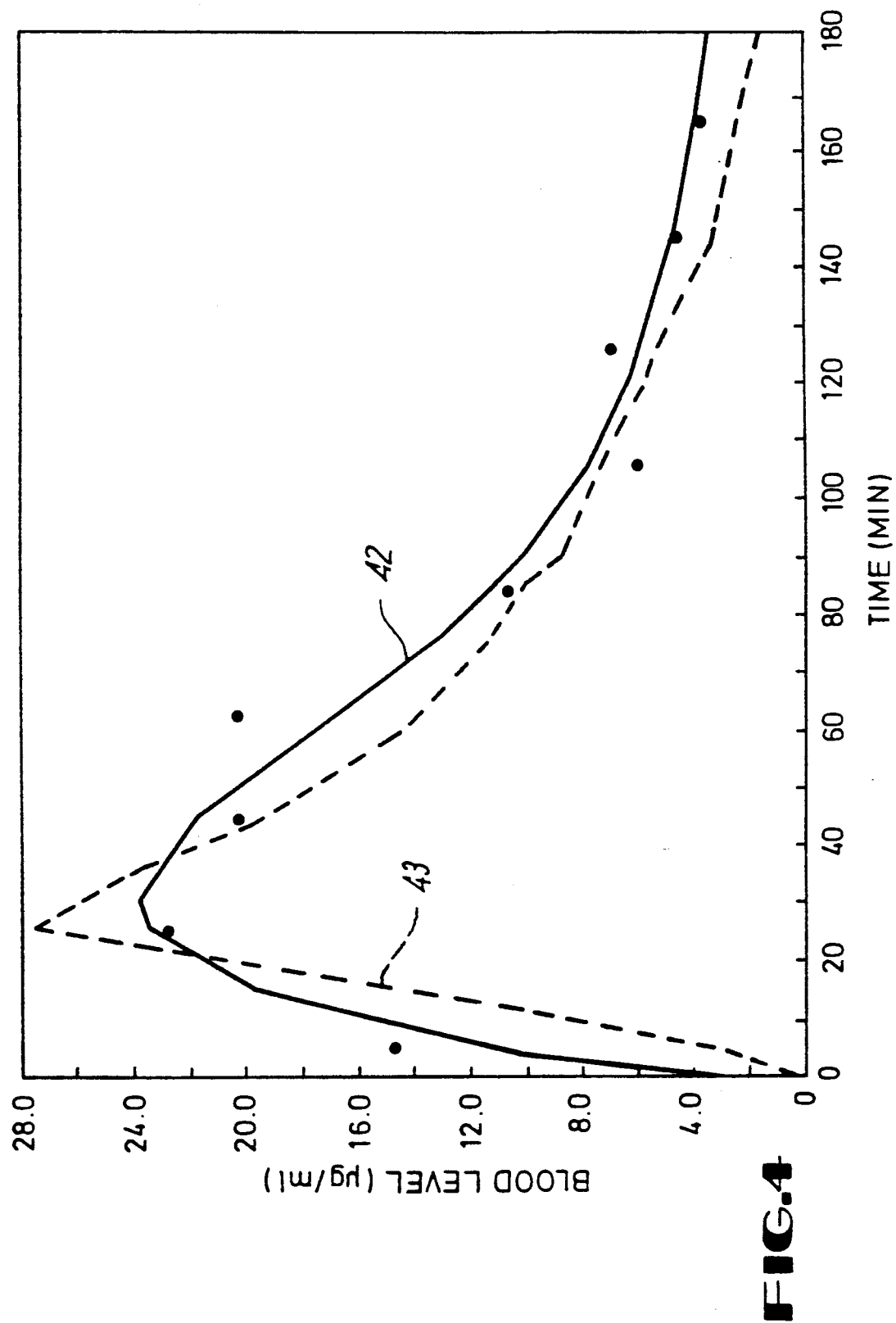
FIG. 4 is a graph comparing the results of the present invention with a known analysis technique.

FIG. 4 is a graph of an in vivo pharmacokinetic analysis using the present invention, compared with a prior art analytical technique.

A 330 gram rat was injected with a dose of 15 milligrams of sodium penicillin G dissolved in 0.3 milliliters of physiological saline solution. Negative ions were recorded in the mass spectrometric analysis of the dialysate in order to obtain maximum sensitivity. FIG. 4 shows the time-dependent rise and fall in the concentration of free drug (non-protein bound) in the rat following injection of the drug. The solid curve 42 was produced using a non-linear least squares fit of the data points shown obtained using the present invention. The drug peaked at a concentration of approximately 24 micrograms per milliliter at about 30 minutes. This peak-time is in good agreement with published data (*The Pharmacological Basis of Therapeutics*, fifth edition, MacMillan, (1975), p. 1130), which has reported the intramuscular administration of this antibiotic to peak in about 26–30 minutes, as shown by the broken curve 43 in FIG. 4.

A combination of microdialysis and mass spectrometry can be used in a wide variety of applications to provide on-line and direct monitoring of aqueous biological samples including in vivo drug monitoring. In addition, the present invention can be used as a fast and efficient method for simultaneously screening complex biological fluids for several low molecular weight compounds of interest since the molecular weight cut-off of the dialysis membrane used in the microdialysis probe of the present invention will preclude dialysis of proteins and other molecules above about 20,000 daltons. In addition, the present invention can also be used in a clinical laboratory for the direct analysis of body fluids, including the detection of illicit substances such as cocaine. Further, the present invention provides a simple and clean method to sample and monitor enzymic reactions, cell cultures, fermentation processes, or other batch processes where the compound of interest is within the mass and sensitivity range of modern mass spectrometers.

In addition, the present invention is particularly applicable to the continuous monitoring of antibiotic levels in infected tissue to indicate the degree of tissue antibiotic penetration, allowing appropriate therapeutic adjustments of the amount of antibiotic administered. Automatic control of the delivery of the drug using data supplied by the microdialysis/mass spectrometry of the present invention is also an important aspect. The monitored antibiotic levels are preferably maintained consistently above those levels necessary for bacterial growth inhibition, and below the toxic levels for the selected antibiotic, thereby enhancing the potential for an early resolution of the infectious process.

What is claimed is:

1. An apparatus for measuring specific biological compounds in a living animal, comprising:

an implantable microdialysis probe having a channel with a perfusate input and a dialysate output, said channel including a dialyzing membrane;

a continuous source of perfusate connected to said perfusate input;

mass spectrometer means for measuring an amount of specific biological compounds in said dialysate; and switch valve means, connected between said dialysate output and said mass spectrometer means, positionable in a first position to collect dialysate and positionable in a second position to transfer collected dialysate to said mass spectrometer means.

2. The apparatus of claim 1, further comprising:

means, connected to said mass spectrometer means, for administering a drug to a live animal according to said amount of said specific biological compounds in said dialysate.

3. The apparatus of claim 1, wherein said mass spectrometer means is a continuous flow fast atom bombardment mass spectrometer.

* * * * *